United States Patent
Lo et al.

(10) Patent No.: US 7,214,840 B2
(45) Date of Patent: May 8, 2007

(54) REDUCTION OF THE BROMINE INDEX OF LINEAR ALKYLBENZENES

(75) Inventors: Frederick Y. Lo, Middlesex, NJ (US); David L. Stern, Baton Rouge, LA (US); Ronald J. Cimini, Friendswood, TX (US); James L. Propp, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 250 days.

(21) Appl. No.: 10/897,528

(22) Filed: Jul. 23, 2004

(65) Prior Publication Data

US 2006/0020154 A1   Jan. 26, 2006

(51) Int. Cl.
    *C07C 2/68* (2006.01)
(52) U.S. Cl. ................ 585/323; 585/809
(58) Field of Classification Search ........ 585/323, 585/809
    See application file for complete search history.

(56) References Cited

U.S. PATENT DOCUMENTS

| | | | |
|---|---|---|---|
| 4,433,196 A | 2/1984 | Yang et al. | 585/823 |
| 4,795,550 A | 1/1989 | Sachtler et al. | 208/307 |
| 6,031,144 A | 2/2000 | Campbell et al. | 585/449 |
| 6,069,285 A * | 5/2000 | Fritsch et al. | 585/449 |
| 6,169,219 B1 | 1/2001 | Kojimi et al. | 585/449 |

FOREIGN PATENT DOCUMENTS

| | | |
|---|---|---|
| EP | 0 895 977 | 2/1999 |
| WO | WO 99/38936 | 8/1999 |
| WO | WO 01/30942 | 5/2001 |

* cited by examiner

*Primary Examiner*—Thuan Dinh Dang
(74) *Attorney, Agent, or Firm*—Darryl M. Tyus

(57) ABSTRACT

In a process for reducing the Bromine Index of a feed containing a linear alkylbenzene and bromine-reactive olefinic hydrocarbon contaminants, the feed is contacted under conditions effective to remove bromine-reactive olefinic hydrocarbon contaminants with a catalyst comprising zeolite Y catalyst having an alpha value of about 2 to about 30. The feed will normally also contain benzene and linear paraffin remaining from the alkylation process used to produce the linear alkylbenzene.

10 Claims, No Drawings

REDUCTION OF THE BROMINE INDEX OF LINEAR ALKYLBENZENES

FIELD

This invention relates to a process for the reduction of the Bromine Index of linear alkylbenzenes and a process for producing a linear alkylbenzene.

BACKGROUND

In many organic compounds, such as linear alkylbenzenes, trace amounts of unsaturation can cause undesirable by-products in downstream reactions. Since the exact nature of the unsaturation may vary and may even be unknown, indirect methods of measuring unsaturation are typically used. One well-known method of measuring trace unsaturation is the Bromine Index and is based on the fact that any chemical that can react with bromine at 0° C. in less than 15 minutes will cause an increase in Bromine Index. The measurement of Bromine Index is described in detail in ASTM D2710, the entire contents of which are incorporated herein by reference. The Bromine Index indirectly measures the olefin content of aromatic containing hydrocarbon samples using potentiometric titration. Specifically, the Bromine Index is defined as the number of milligrams of bromine consumed by 100 grams of hydrocarbon sample.

Linear alkylbenzenes are used in the commercial production of detergents by a process involving sulfonation. In this process, excessive unsaturation in the linear alkylbenzene can result in undesirable discoloration of the detergent, typically as measured by its Klett color rating. As a result, linear alkylbenzenes used in detergent production are typically required to have a Bromine Index less than 10.

Linear alkylbenzenes are typically produced by contacting benzene with a long-chain (having more than 10 carbon atoms) alpha-olefin in the presence of a supported acid catalyst or a solid acid catalyst. However, this process frequently produces linear alkylbenzenes with Bromine Index values significantly in excess of 10 and sometimes in excess of 50. Thus additional processing to reduce the Bromine Index may be required.

Clays have been used for many years in the commercial treatment of organic products, such as paraffins, benzene, toluene and xylene, to reduce their Bromine Index. However, linear alkylbenzenes (LAB) are much larger molecules with higher molecular weight and the residual olefinic compounds can be highly substituted such that the activation of the olefinic group is sterically hindered. As a result, the treatment of LAB product with clays has resulted in relatively low catalyst activity and short cycle life at low temperatures and excessive cracking activity at higher temperatures resulting in lower yield of LAB after treatment.

More recently, zeolites, and particularly large pore zeolites, have been proposed as replacements for clays in the removal of bromine reactive contaminants from organic feedstocks. Thus, for example U.S. Pat. No. 4,795,550 discloses the use of aluminosilicate zeolites to remove trace olefins from aromatic and naphthenic feedstocks so as to reduce the Bromine Index of the feedstocks from initial values of 50 to 2000 to final values of 0.1 to 50. Among the feedstocks mentioned as suitable in the '550 patent are $C_{16}$ to $C_{20}$ linear alkylbenzenes.

U.S. Pat. No. 6,031,144 discloses a two-step process for reducing the residual olefin content of an alkylation reaction product of a single-ring aromatic hydrocarbon with an at least $C_{16}$ olefin in which at least a portion of a non-alkylated single-ring aromatic hydrocarbon is removed in a first step; followed by a second step in which the remaining reaction product is reacted in the presence of an acidic catalyst to produce a final alkylation reaction product having reduced olefin content.

U.S. Pat. No. 6,169,219 discloses a multi-stage process for producing linear alkylbenzenes in which benzene is alkylated with a $C_6$ to $C_{20}$ linear olefin in a first alkylation stage with a first fluorided silica-alumina catalyst at a first temperature and then at least part of the first alkylation stage effluent is reacted in a second alkylation stage with a second fluorided silica-alumina catalyst at a second temperature higher than the first temperature. The second alkylation stage converts polymeric by-products in the first alkylation stage effluent to heavy alkylate which is separated from the LAB product in a downstream separation step.

According to the invention, it has now been found that a catalyst which contains zeolite Y catalyst which has an alpha value of 2 to 30 is particularly effective in reducing the Bromine Index of linear alkylbenzene products, especially in the presence of the benzene and n-paraffin impurities conventionally present in the direct effluent of an LAB manufacturing plant. Thus, using the process of the invention, it has been possible to reduce the Bromine Index of a linear alkylbenzene product from in excess of 80 to less than 10 using zeolite Y catalyst, or preferably an ultrastable zeolite Y (USY) catalyst.

SUMMARY

In one aspect, the invention resides in a process for reducing the Bromine Index of a feed containing a linear alkylbenzene and bromine-reactive olefinic hydrocarbon contaminants, comprising the step of contacting the feed under reaction conditions effective to remove bromine-reactive olefinic hydrocarbon contaminants with a catalyst comprising zeolite Y catalyst having an alpha value of about 2 to about 30.

Preferably, the catalyst comprises zeolite Y catalyst having an alpha value of about 10 to about 20.

Preferably, the catalyst comprises zeolite Y catalyst having a silica/alumina molar ratio of about 5 to about 100 and more preferably of about 10 to about 30.

Preferably, said reaction conditions include a temperature of about 75° C. to about 300° C. and more preferably about 125° C. to about 225° C.

Preferably, the feed also contains benzene and a normal paraffin having the same number of carbon atoms as the alkyl group of the linear alkylbenzene.

In a further aspect, the invention resides in a process for producing a linear alkylbenzene comprising the steps of:
  (a) alkylating benzene under suitable alkylation conditions with a linear olefin produced by dehydrogenation of a normal paraffin to produce an alkylation effluent containing a linear alkylbenzene, benzene and said normal paraffin, and then
  (b) without separating the benzene and said normal paraffin from said alkylation effluent, contacting said effluent under conditions effective to remove bromine-reactive olefinic hydrocarbon contaminants with a catalyst comprising zeolite Y catalyst having an alpha value of about 2 to about 30.

Preferably, the suitable alkylation conditions include a temperature of from about 0° C. to about 500° C., a pressure of from about 0.2 to about 250 atmospheres, a feed weight hourly space velocity (WHSV) of from about 0.1 $hr^{-1}$ to about 500 $hr^{-1}$ and an aromatic compound to olefinic hydrocarbon mixture mole ratio of from about 1:1 to about 20:1.

Preferred reaction conditions include a temperature within the range of from about 100° C. to about 350° C., a pressure of from about 1 to about 25 atmospheres, a feed WHSV of from about 0.5 hr$^{-1}$ to about 100 hr$^{-1}$ and an aromatic compound to olefinic hydrocarbon mixture mole ratio of from about 4:1 to about 15:1.

Prefereably, the conditions under which the zeolite Y catalyst contacts the alkylation effluent containing the linear alkylbenzene feed in the process of the invention typically comprise a temperature of about 75° C. to about 300° C., a liquid hourly space velocity of from about 0.5 to about 10 hr$^{-1}$, and a pressure sufficient to maintain the process stream in the liquid phase at a pressure greater than 1 atmosphere (100 kPa). In one embodiment, the temperature employed is about 125° C. to about 225° C., such as from 150° C. to 180° C. Under these conditions the zeolite Y catalyst is effective to remove the bromine-reactive olefinic hydrocarbon contaminants in the feed without excessive side reactions such as cracking, disproportionation and/or transalkylation. In this way, preferably the Bromine Index of a feed having a Bromine Index of less than about 50 may be most preferably reduced to less than about 10.

Preferably, the process includes the further step of subjecting the product of step (b) to clay treatment.

DETAILED DESCRIPTION OF THE EMBODIMENTS

The present invention is directed to a process for reducing the Bromine Index of a feed containing a linear alkylbenzene and bromine-reactive olefinic hydrocarbon contaminants, particularly wherein the feed is the effluent from a linear alkylbenzene production process in which benzene is alkylated with a linear olefin preferably obtained by dehydrogenation of a normal paraffin. In such a case the catalyst employed in the process of the invention can be used as a tail bed directly following the alkylation catalyst bed or can be used in a separate reaction vessel downstream of the alkylation reaction vessel but before any distillation/purification steps. Using this catalyst to reduce Bromine Index of the linear alkylbenzene before the distillation and purification steps has the advantage of suppressing the undesirable reactions of cracking, disproportionation and transalkylation that could take place in the presence of a strong acid catalyst.

The process of the present invention is generally applicable to any linear alkylbenzene in which the alkyl group has 6 to 20 carbon atoms, but preferably is employed with linear alkylbenzenes having 8 to 16, and more preferably 10 to 14, carbon atoms.

As indicated above, the linear alkylbenzene feed used in the present invention is preferably produced by alkylation of benzene with a linear olefin, typically having 6 to 20 carbon atoms, produced by dehydrogenation of the corresponding n-paraffin under conditions which minimize the formation of branched olefins. Paraffin dehydrogenation is well-known in the art and hence need not be discussed in detail herein, but further information on this process can be found in R. A. Meyers, "Handbook of Petroleum Refining Processes", McGraw-Hill Book Company (1986), 4–36 to 4–38; Ullman's Encyclopedia of Industrial Chemistry, 5th Ed., V. A. 13, Verlagsgesellschaft mbH (1989) pp. 234, 242–243; Kirk-Othmer Encyclopedia of Chemical Technology, 3rd Ed., V. 16, J. Wiley & Sons (1981) p. 492; "Encyclopedia of Chemical Processing and Design", J. J. McKetta, Editor, V. 14, M. Dekker, Inc., (1982) pp. 276–289.

Alkylation of benzene with linear olefins to produce linear alkylbenzenes is also well known in the art, see R. A. Meyers, op. cit., 1–39 to 1–41; Ullman's Encyclopedia of Industrial Chemistry, op cit., V. A13, pp. 259–260. Although liquid hydrogen fluorine (HF) long has been the catalyst of choice, solid alkylation catalysts have been known for some time and are gaining favor as the environmental concerns regarding HF become more important. Many solid materials having activity as alkylation catalysts are well known and include materials such as silica-aluminas, crystalline aluminosilicates such as zeolites and molecular sieves, naturally occurring and synthetic clays, including pillared clays, sulfated oxides such as sulfated zirconia, traditional Friedel-Crafts catalysts, such as aluminum chloride and zinc chloride, and solid Lewis acids generally. Preferably, the alkylation catalyst is a molecular sieve selected from the group consisting of MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575), and MCM-56 (described in U.S. Pat. No. 5,362,697), the entire contents of which are incorporated herein by reference.

Suitable alkylation conditions include a temperature of from about 0° C. to about 500° C., a pressure of from about 0.2 to about 250 atmospheres, a feed weight hourly space velocity (WHSV) of from about 0.1 hr$^{-1}$ to about 500 hr$^{-1}$ and an aromatic compound to olefinic hydrocarbon mixture mole ratio of from about 1:1 to about 20:1. Preferred reaction conditions include a temperature within the range of from about 100° C. to about 350° C., a pressure of from about 1 to about 25 atmospheres, a feed WHSV of from about 0.5 hr$^{-1}$ to about 100 hr$^{-1}$ and an aromatic compound to olefinic hydrocarbon mixture mole ratio of from about 4:1 to about 15:1.

The effluent from the alkylation process described above may contain in addition to the desired linear alkylbenzene, unreacted benzene, the n-paraffin precursor of the linear olefin used in the alkylation step, as well as various unidentified bromine-reactive olefinic hydrocarbon contaminants. As used herein, the term "bromine-reactive olefinic hydrocarbon contaminates" includes mono- and di-unsaturated oliphatic hydrocarbons of varying carbon number. In accordance with the invention the entire effluent from the alkylation step, without any intermediate distillation and/or purification, is treated with a zeolite Y catalyst, such as zeolite USY catalyst which is effective to remove the bromine-reactive contaminants without excessive cracking, disproportionation and/or transalkylation of the linear alkylbenzene product.

Preferably, the Bromine Index of the linear alkylbenzene feed or alkylation effluent prior to contacting with zeolite Y catalyst is preferably less than about 50, more preferably less than about 30, and most preferably less than about 20. After contacting such feed or alkylation effluent with zeolite Y catalyst in accordance with invention, the Bromine Index is preferably reduced to less than about 20, more preferably less than about 15, and most preferably less than about 10.

The zeolite Y catalyst employed is selected so as to have a moderate acid activity as measured by an alpha value of about 2 to about 30, more preferably of about 10 to about 20, and most preferebly from about 15 to about 20. Alpha Value is well known in the art and is an approximate indication of the catalytic cracking activity of the catalyst compared to a standard catalyst. It gives the relative rate constant (rate of normal hexane conversion per volume of catalyst per unit time) and is based on the activity of a silica-alumina cracking catalyst taken as an Alpha of 1 (Rate Constant=0.016 sec$^{-1}$). The Alpha Test is described in U.S. Pat. No. 3,354,078, in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395.

Preferably, the zeolite Y catalyst employed is zeolite USY catalyst (ultrastable zeolite Y catalyst) having a silica/alumina molar ratio of about 5 to about 100 and more preferably of about 10 to about 30. (Zeolite USY is commercially available but are described in, for example, U.S. Pat. Nos. 3,293,192 and 3,449,070, the entire contents of which are incorporated herein by reference.

When used in the process of the invention, the zeolite Y catalyst is preferably combined with another material resistant to the temperatures and other conditions employed in process. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material which is active tends to change the conversion and/or selectivity of the catalyst in the process. Inactive materials suitably serve as diluents to control the amount of conversion in the process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the zeolite Y catalyst include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite Y catalyst also include inorganic oxides, such as silica, zirconia, titania, magnesia, beryllia, alumina, and mixtures thereof.

In addition to the foregoing materials, the zeolite Y catalyst component can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of zeolite Y catalyst component and inorganic oxide matrix may vary widely, with the zeolite Y catalyst content ranging from about 1 to about 90 percent by weight and more usually, in the range of about 2 to about 80 weight percent of the composite.

The conditions under which the zeolite Y catalyst contacts the linear alkylbenzene feed in the process of the invention typically comprise a temperature of about 75° C. to about 300° C., a liquid hourly space velocity of from about 0.5 to about 10 hr$^{-1}$, and a pressure sufficient to maintain the process stream in the liquid phase at a pressure greater than 1 atmosphere (100 kPa). In one embodiment, the temperature employed is about 125° C. to about 225° C., such as from 150° C. to 180° C. Under these conditions the zeolite Y catalyst is effective to remove the bromine-reactive olefinic hydrocarbon contaminants in the feed without excessive side reactions such as cracking, disproportionation and/or transalkylation. In this way, the Bromine Index of the feed can be reduced from in excess of 20 to less than 10.

The process of the invention can optionally include a final clay-treatment step to treat the linear alkylbenzene product after contacting with the zeolite Y catalyst. Since the Bromine Index of the product is already significantly reduced to a very low level, the life cycle of the clay bed will be significantly longer than in conventional clay treatment processes.

The invention will now be more particularly described with reference to the following Examples.

EXAMPLES 1–14

A series of experiments were conducted to test the efficiency of various clay and zeolite catalysts in reducing the Bromine Index of a linear alkylbenzene product (LAB product) prepared by the alkylation of benzene with $C_{10}$ to $C_{14}$ olefins using an MCM-22 catalyst. The LAB contained about 85 wt % of 2- and 3-phenyl isomers and had a Bromine Index of 87.

Prior to use in the experiments, the as-received LAB product was passed through an alumina/13× gas chromatography column and then stored in a closed container to avoid air and moisture exposure. In addition, a mixture composed of 33.33 wt % benzene and 66.67 wt % dodecane was prepared and passed through another alumina/13× gas chromatography column and stored in a clean dry container under nitrogen. This mixture was intended to represent the impurities expected to be present in a commercial LAB stream.

The catalysts used in the experiments were as follows:
Examples 1–5—65 wt % USY/35 wt % alumina catalyst with alpha value of 17;
Example 6—90 wt % USY/10 wt % silica catalyst with alpha value of 1;
Example 7—$WO_x/ZrO_2$ (see U.S. Pat. No. 5,510,309);
Example 8—Engelhard F24 clay;
Example 9—65 wt % zeolite beta/35 wt % alumina catalyst (alpha value 210);
Example 10—65 wt % zeolite beta/35 wt % alumina catalyst (alpha value 37);
Example 11—65 wt % MCM-22/35 wt % alumina catalyst;
Example 12—80 wt % MCM-49/20 wt % alumina catalyst;
Example 13—65 wt % MCM-41/35 wt % alumina catalyst (alpha value 1);
Example 14—100 wt % CaECR-34 (in powder form) catalyst;
Further details of the catalysts are listed in Tables 1 and 2 below.

In each experiment, the catalyst to be tested was screened through a 14–20 mesh screen, dried at 120° C. overnight and then 12 grams (3 grams in Example 5) of the dried catalyst were loaded into a reactor. 150 cc of the purified benzene/dodecane mixture were then added to the reactor, the reactor was purged with nitrogen and then heated with agitation at 600 rpm to a selected temperature between 150 and 210° C. While reactor was heating up, 45 cc of LAB was weighed into a hoke vessel, the vessel was then purged with nitrogen and connected to an inlet port of the reactor. The upper end of the hoke vessel was connected to a source nitrogen pressure at about 200 psig and the contents of the hoke vessel were forced into the reactor under the nitrogen pressure.

Samples (10 cc) of the reactor contents were taken prior to, and then 10, 30, 60 and 120 minutes after, addition of the LAB and the Bromine Index (BI) of the samples were measured by ASTM D2710. The results are listed in Tables 1 and 2.

From the results in Tables 1 and 2, it will be seen that the moderate alpha value zeolite USY catalyst of Examples 1 and 2 exhibited enhanced Bromine Index reduction activity as compared with the F24 clay catalyst of Example 8 over the entire temperature range tested, 150–210° C., particularly in the presence of the benzene/dodecane mixture. Moreover, the acid wash color of the product in Example 1 was lower (indicating less undesirable coloration) than that obtained using the clay catalyst of Example 8. In contrast, the low alpha value zeolite USY catalyst of Example 6 showed lower activity for Bromine Index reduction than did the clay catalyst of Example 8. In fact, apart from the MCM-49 catalyst of Example 12 (which performed similarly to the clay catalyst) all the other molecular sieve catalysts tested were less effective in reducing the Bromine Index of the LAB sample of the clay catalyst of Example 8.

TABLE 1

| | Example | | | | | | |
|---|---|---|---|---|---|---|---|
| | 1 | 2 | 3 No LAB | 4 100% LAB | 5 3 g cat | 6 | 7 |
| Catalyst | USY-30 | USY-30 | USY-30 | USY-30 | USY-30 | USY-2 | $WO_x/ZrO_2$ |
| Alpha | 17 | 17 | 17 | 17 | 17 | 1 | 1 |
| SA, m2/g | ~544 | ~544 | ~544 | ~544 | ~544 | 836 | 81 |
| PV, cc/g | ~0.89 | ~0.89 | ~0.89 | ~0.89 | ~0.89 | 0.76 | |
| Pore diameter, A | 7.4 × 7.4 | 7.4 × 7.4 | 7.4 × 7.4 | 7.4 × 7.4 | 7.4 × 7.4 | 7.4 × 7.4 | N/A |
| Si/Al ratio | ~15 | ~15 | ~15 | ~15 | ~15 | ~200 | N/A |
| Temperature ° C. | 150 | 180–210 | 150 | 150 | 150 | 150–210 | 150 |
| BI before LAB addition | 4.0 | 0.3 | 2.34 | 88.6 | 8.89 | 5.0 | 3.9 |
| BI after LAB addition | 23.5 | 20.8 | No LAB | 84.02 | 27.1 | 24.3 | 23.5 |
| BI at 10 min | 16.4 | 8.6 | 5.49 | 71.07 | | 22.9 | 19.1 |
| BI at 30 min | 12.3 | | 1.35 | 49.22 | 20.42 | 19.0 | 16.0 |
| BI at 60 min | 8.2 | 11.9 | 2.17 | 43.97 | 22.38 | 18.3 | 13.0 |
| BI at 120 min | 5.4 | 2.7 | 3.63 | 32 | 25.47 | 13.5 | 12.9 |
| BI at 180 min | — | 6.2 | — | | 15.85 | | |
| BI at 240 min | | | | | 10.89 | | |
| Acid Wash Color (ASTM D848) | 1 | >5 | | | | | 3 |
| GC analysis at end of run | | | | | | | |
| Mono-Substituted Benzenes (wt %) | 99.78 | 94.65 | | | | | 98.18 |
| Di-Substituted Benzenes (wt %) | 0.20 | 5.27 | | | | | 1.76 |
| Tri-Substituted Benzenes (wt %) | 0.02 | 0.08 | | | | | 0.06 |

TABLE 2

| | Example | | | | | | |
|---|---|---|---|---|---|---|---|
| | 8 | 9 | 10 | 11 | 12 | 13 | 14 |
| Catalyst | F24 | Beta | Beta | MCM-22 | MCM-49 | MCM-41 | ECR-34 |
| Alpha | 0.2 | 210 | 37 | | | ~1 | |
| SA, m2/g | 337.00 | ~400 | ~400 | | | ~622 | |
| PV, cc/g | 0.44 | | | | | ~1.4 | |
| Pore diameter, Ang | 100–200 | 7.6 × 6.4 5.5 × 5.5 | 7.6 × 6.4 5.5 × 5.5 | | | 50 | |
| Si/Al ratio | N/A | ~30–50 | ~30–50 | | | pure $SiO_2$ | |
| Temperature, ° C. | 180 | 150 | 150 | 150–180 | 150 | 150–180 | 150 |
| BI before LAB addition | 14.6 | 17.2 | 6.5 | 5.94 | 0 | 10.1 | 9.26 |
| BI after LAB addition | 31.5 | 33.8 | 25.4 | 25.3 | 20.8 | 28.0 | 25.3 |
| BI at 10 min | 18.0 | 28.4 | 17.3 | 20.22 | 17.87 | 31.2 | — |
| BI at 30 min | 12.0 | 26.2 | 14.5 | 19.54 | 8.33 | 26.7 | — |
| BI at 60 min | 8.9 | 22.7 | 12.0 | 20.86 | 8.98 | 24.9 | 25.35 |
| BI at 120 min | 7.2 | 22.3 | 13.2 | 17.86 | 7.39 | 23.6 | 34.6 |
| BI at 180 min | — | — | — | 20.55 | | 26.5 | 11 |
| BI at 240 min | | | | | | | |
| Acid Wash Color (ASTM D848) | 5 | | | | | | |
| GC analysis at end of run | | | | | | | |
| Mono-Substituted Benzenes (wt %) | 95.35 | | | | | | |
| Di-Substituted Benzenes (wt %) | 4.53 | | | | | | |
| Tri-Substituted Benzenes (wt %) | 0.12 | | | | | | |

EXAMPLES 15–19

In another series of experiments, Examples 15 to 18, the process of the preceding Examples was repeated with a zeolite USY catalyst similar to that used in Examples 1 to 5 (including a different manufacturing batch) which was dried or calcined at different temperatures from 120 to 540° C. (250° F. to 1000° F.). The results are summarized in the Table 3 and indicate that a freshly calcined catalyst from rotary calciner give very high activity in reducing the Bromine Index and still maintains very little loss of LAB.

Example 19 was run at higher temperature of 180° C. using only 3 grams of catalyst instead of 12 grams, and the feedstock consisted of 122.2 grams of benzene and 61.1 g of LAB and no dodecane as a diluent. Results from Example 19, together with those of Example 2, are given in Table 4 and illustrate that the reaction can be conducted at temperatures of 180° C. and higher with very little loss of LAB.

TABLE 3

| | Results | | | | |
|---|---|---|---|---|---|
| | Same catalyst batch as in Examples 1 to 5 | | | MZ-20 | MZ-20 |
| Catalyst drying or calcination conditions | 120° C. | 260° C. | 120° C. | 540° C. (Furnace) | 540° C. (Rotary Calciner) |
| Examples # | 1 | 15 | 16 | 17 | 18 |
| Catalyst | USY-30 | USY | USY-30 | USY-30 | USY-30 |
| Alpha | 17 | | | | |
| Temperature in ° C. | 150 | 150 | 150 | 150 | 150 |
| BI before LAB addition | 4.0 | 1.41 | 4.57 | 4.04 | 3.32 |
| BI after LAB addition | 23.5 | | | | |
| BI at 10 min | 16.4 | 11.97 | 15.07 | 12.64 | 7.85 |
| BI at 30 min | 12.3 | 7.75 | 13.35 | 8.99 | 5.34 |
| BI at 60 min | 8.2 | 6.28 | 11.78 | 8.75 | 2.76 |
| BI at 120 min | 5.4 | 7.35 | 7.8 | 6.07 | 1.38 |
| BI at 180 min | — | | | | |
| GC analysis at end of run | | | | | |
| Mono-Substituted Benzenes wt % | 99.78 | 99.41 | 99.83 | 99.75 | 99.55 |
| Di-Substituted Benzenes wt % | 0.20 | 0.55 | 0.15 | 0.21 | 0.45 |
| Tri-Substituted Benzenes wt % | 0.02 | 0.04 | 0.03 | 0.02 | 0.00 |

TABLE 4

| | Results | |
|---|---|---|
| | 12 g Catalyst | 3 g Catalyst |
| Examples # | 2 | 19 |
| Catalyst | USY-30 | USY |
| Alpha | 17 | |
| Temperature in ° C. | 180–210 | 180 |
| BI before LAB addition | 0.3 | 2.71 |
| BI after LAB addition | 20.8 | |
| BI at 10 min | 8.6 | |
| BI at 30 min | | 25.40 |
| BI at 60 min | 11.9 | 20.82 |
| BI at 120 min | 2.7 | 11.84 |
| BI at 180 min | 6.2 | 9.82 |
| GC analysis at end of run | | |
| Mono-Substituted Benzenes wt % | 94.65 | 99.66 |
| Di-Substituted Benzenes wt % | 5.27 | 0.33 |
| Tri-Substituted Benzenes wt % | 0.08 | 0.01 |

We claim:

1. A process for producing a linear alkylbenzene comprising the steps of:
   (a) alkylating benzene with a linear olefin produced by dehydrogenation of a normal paraffin to produce an alkylation effluent containing a linear alkylbenzene, benzene and said normal parffin, and then
   (b) without separating the benzene and said normal paraffin from said alkylation effluent, contacting said effluent with a catalyst comprising zeolite Y catalyst having a silica/alumina molar ratio of 5 to 100 and an alpha value of about 10 to about 20 under conditions effective to reduce the amount of bromine-reactive olefinic hydrocarbon contaminants; wherein said conditions include a temperature in the range of from 75° C. to 180° C.

2. The process of claim 1, wherein the Bromine Index of the feed after the contacting step is less than about 20.

3. The process of claim 1, wherein the Bromine Index of the feed after the contacting step is less than about 15.

4. The process of claim 1, wherein the Bromine Index of the feed after the contacting step is less than about 10.

5. The process of claim 1, wherein step (a) is conducted under conditions including a temperature of from about 0° C. to about 500° C., a pressure of from about 0.2 to about 250 atmospheres (20 to 25,000 kPa), a feed weight hourly space velocity (WHSV) of from about 0.1 hr$^{-1}$ to about 500 hr$^{-1}$ and an aromatic compound to olefinic hydrocarbon mixture mole ratio of from about 1:1 to about 20:1.

6. The process of claim 1, wherein step (a) is conducted under conditions including a temperature within the range of from about 100° C. to about 350° C., a pressure of from about 1 to about 25 atmospheres (100 to 2,500 kPa), a feed WHSV of from about 0.5 hr$^{-1}$ to about 100 hr$^{-1}$ and an aromatic compound to olefinic hydrocarbon mixture mole ratio of from about 4:1 to about 15:1.

7. The process of claim 1, wherein step (b) is conducted under conditions including a liquid hourly space velocity of from about 0.5 to about 10 hr$^{-1}$, and a pressure of about greater than 1 atmosphere (100 kPa).

8. The process of claim 7, wherein said conditions in step (b) include a temperature of about 125° C. to 180° C.

9. The process of claim 7, wherein said conditions in step (b) include a temperature of about 150° C. to about 180° C.

10. The process of claim 1 and including the further step of subjecting the product of step (b) to clay treatment.

* * * * *